US009668956B2

(12) United States Patent
Koshti et al.

(10) Patent No.: US 9,668,956 B2
(45) Date of Patent: Jun. 6, 2017

(54) LOW VISCOUS, SULFATE-FREE COLD-DISPERSIBLE PEARLESCENT CONCENTRATE

(71) Applicant: GALAXY SURFACTANTS LTD., Navi Mumbai (IN)

(72) Inventors: Nirmal Koshti, Piscataway, NJ (US); Pritesh Rajaram Mhatre, Raigad (IN); Anuradha Sharma, Navi Mumbai (IN)

(73) Assignee: Galaxy Surfactants, Ltd., Maharashtra (IN)

( * ) Notice: Subject to any disclaimer, the term of this patent is extended or adjusted under 35 U.S.C. 154(b) by 39 days.

(21) Appl. No.: 14/715,864

(22) Filed: May 19, 2015

(65) Prior Publication Data
US 2015/0335550 A1 Nov. 26, 2015

(30) Foreign Application Priority Data
May 21, 2014 (IN) .......................... 1697/MUM/2014

(51) Int. Cl.
| | | |
|---|---|---|
| *C11D 1/10* | (2006.01) | |
| *C11D 3/20* | (2006.01) | |
| *C11D 3/30* | (2006.01) | |
| *C11D 3/32* | (2006.01) | |
| *A61K 8/42* | (2006.01) | |
| *A61Q 5/02* | (2006.01) | |
| *A61Q 19/10* | (2006.01) | |
| *C11D 3/00* | (2006.01) | |
| *A61Q 5/10* | (2006.01) | |
| *A61Q 1/14* | (2006.01) | |
| *C11D 1/66* | (2006.01) | |
| *A61K 8/44* | (2006.01) | |

(52) U.S. Cl.
CPC ................ *A61K 8/42* (2013.01); *A61K 8/44* (2013.01); *A61Q 1/14* (2013.01); *A61Q 5/02* (2013.01); *A61Q 5/10* (2013.01); *A61Q 19/10* (2013.01); *C11D 1/10* (2013.01); *C11D 1/66* (2013.01); *C11D 3/0089* (2013.01); *C11D 3/2044* (2013.01); *C11D 3/2093* (2013.01); *C11D 3/32* (2013.01); *A61K 2800/30* (2013.01); *A61K 2800/436* (2013.01)

(58) Field of Classification Search
CPC ........... C11D 1/10; C11D 1/66; C11D 3/2044; C11D 3/0089; C11D 3/2093; C11D 3/32; A61Q 1/14; A61Q 5/02; A61Q 5/10
USPC ....... 510/123, 126, 130, 136, 137, 138, 499, 510/501, 502, 505, 506
See application file for complete search history.

(56) References Cited

U.S. PATENT DOCUMENTS

| | | | | |
|---|---|---|---|---|
| 5,403,508 A | * | 4/1995 | Reng | A61K 8/375 424/70.31 |
| 5,464,106 A | * | 11/1995 | Slat | B29C 49/0073 215/12.1 |
| 5,560,873 A | | 10/1996 | Chen | |
| 5,711,899 A | | 1/1998 | Kawa | |
| 5,925,604 A | * | 7/1999 | Chen | A61K 8/39 510/120 |
| 6,147,124 A | | 11/2000 | Ansmann et al. | |
| 6,210,659 B1 | * | 4/2001 | Wilhelm | A61K 8/44 424/70.1 |
| 6,306,916 B1 | | 10/2001 | Ansmann | |
| 7,578,995 B2 | | 8/2009 | Frantz | |
| 8,263,538 B2 | * | 9/2012 | Tsaur | A61K 8/42 510/159 |
| 8,623,809 B2 | * | 1/2014 | Dahms | A61K 8/39 510/424 |
| 2003/0068292 A1 | * | 4/2003 | Pfaffernoschke | A61K 8/416 424/70.12 |
| 2007/0128144 A1 | * | 6/2007 | Bonastre Gilabert | A61K 8/8117 424/70.13 |
| 2010/0189664 A1 | * | 7/2010 | Castro | A61K 8/731 424/52 |
| 2011/0034366 A1 | * | 2/2011 | Panandiker | C11D 3/40 510/321 |
| 2011/0152159 A1 | * | 6/2011 | Labeque | C11D 3/505 510/296 |
| 2011/0223125 A1 | * | 9/2011 | Hough | A61K 8/8152 424/70.12 |
| 2013/0164356 A1 | * | 6/2013 | Pfaff | A23G 3/343 424/401 |
| 2016/0206537 A1 | * | 7/2016 | Koshti | A61Q 5/02 |

FOREIGN PATENT DOCUMENTS

| | | |
|---|---|---|
| DE | 41 03 551 A1 | 8/1992 |
| EP | 0 205 922 | 12/1986 |
| EP | 0 569 843 A1 | 11/1993 |
| EP | 0 684 302 A1 | 11/1995 |
| JP | 2008-13581 | 1/2008 |
| WO | 94/24248 | 10/1994 |
| WO | 2004/028676 | 4/2004 |
| WO | WO2011/023803 | * 3/2011 |

OTHER PUBLICATIONS

Crombie, Cold Pearl Surfactant-Based Blends, Int'l. Journal of Cosmetic Science, vol. 19, 205-214 (1997).
Regan, A Novel Glycinate-based Body Wash, The Journal of Clinical and Aesthetic Dermatology, vol. 6, No. 6, Jun. 2013.
Kohler, "Microstructure and Dynamics of Worklike Micellar Solutions Formed by Mixing Cationic and Anionic Surfactants", J. Phys. Chem., B 2000, 104, 11035-11044.

* cited by examiner

Primary Examiner — Gregory R Delcotto
(74) Attorney, Agent, or Firm — Kramer Amado P.C.

(57) ABSTRACT

Low viscous, sulfate-free, cold-dispersible, aqueous pearlescent concentrates are prepared. The pearlizing concentrates of the instant invention are stable and remain pumpable and flowable during storage for longer duration.

5 Claims, No Drawings

LOW VISCOUS, SULFATE-FREE COLD-DISPERSIBLE PEARLESCENT CONCENTRATE

FIELD OF INVENTION

The present invention relates to free-flowing, pumpable, low viscosity aqueous pearlescent concentrates. In particular the present invention relates to low viscosity, pearlescent concentrates containing sulfate-free surfactants, particularly salts of N-acyl amino acid surfactants. The present pearlescent concentrates find application in sulfate-free personal care formulations. These concentrates have low viscosity and there is no viscosity build-up on storage for a longer duration of time. The low viscous concentrates show very good rheological stability.

BACKGROUND OF INVENTION

Pearlizers are a long-established and proven medium for providing cosmetic products with an aesthetically attractive, rich and interesting appearance (Cold pearl surfactant-based blends, Crombie, R. L. International Journal of Cosmetic Science, 1997, 19: 205-214).

Typically, all cold-dispersible pearlescent concentrates are made of three components, a) pearly waxes b) surfactants and c) water. Suitable pearlisers or waxes are, for example, the monoesters and diesters of ethylene glycol, propylene glycol and oligomeric alkylene glycols of this type or glycerol with C16-22 fatty acids, fatty acids and also monoalkanolamides of fatty acids with $C_2$ or $C_3$ alkanolamines. Waxes are emulsified with surfactants in aqueous medium and then are gradually allowed to crystallize in the surfactant environment. This process results in a stable uniform dispersion of platelet like structures that reflect light.

The surfactants that are used to disperse the pearly waxes are from all categories, namely, anionic, cationic, amphoteric, zwitterionic and non-ionic (U.S. Pat. Nos. 5,560,873, 5,711,899, 6,147,124, & 7,578,995). Alkyl sulfates and alkyl ether sulfates are known for being harsh on both skin and hair. In fact sodium lauryl sulfate is taken as a standard irritant for irritancy measurement. Sodium lauryl ether sulfate (SLES) is made by sulphating ethoxylated lauryl alcohol of varying degree of ethylene oxide (0.5 to 3.0 moles of EO per one mole of fatty alcohol). Any grade of SLES that is available in the market contains significant amount of sodium lauryl sulfate (more than 20%) that is an established irritant to human skin and mucosa. In the class of anionic surfactants 'sulfates' in general are known to be the highest irritants compared to 'sulphonates or sulphosuccinates'. While doing the cleansing job, alkyl ether sulfates strip away proteins and lipids of cuticle of hair and stratum corneum of skin. Skin's moisture regulation mechanism is seriously affected due to adverse action of harsh surfactants on the proteins and lipids of upper layers of stratum corneum.

Products 'without sulfates' have been launched that do less or no damage to hair. An example of this is L'Oreal's 'sulfate-free' 'Everpure' range of shampoos. Unilever's Dove range of body washes uses mild surfactants like cocoyl isethionate and sodium glycinate to reduce damaging effect of harsh surfactants like fatty alcohol ether sulfates (Nutrium technology, A novel glycinate-based body wash, K. P. Ananthapadmanabhan et al., Journal of Clinical Aesthetic Dermatology 23-30, 6(6), 2013). These rinse-off formulations being sulfate-free require sulfate-free pearlisers to improve the aesthetics.

In addition to the complex requirement profile which these formulations have to satisfy such as high brilliance, good particle fineness and high compatibility with other auxiliaries is the need of performance requirements relating to processability. Particularly, highly concentrated formulations intended for subsequent processing are expected to combine uniform, good physicochemical stability with low viscosity and flowability.

One of the problems involved in the production and use of pearlescent concentrates concerns their flowability and pumpability. In addition, the concentrates may even assume the form of mixtures which do not flow and also cannot be pumped by conventional equipment. Pearlescent concentrates that are commercially available undergo rheological changes during storage period resulting into low shelf life and serious difficulty in handling the non-flowable viscous material. This is reported in the technical data sheets of commercially available cold pearlescent concentrates, for example, Mackpearl series from Rhodia (Solvay) & Euperlan series from Cognis (BASF) wherein it is specified that outside the temperatures range of 15° C. and 35° C. the pumpability may be restricted due to an increase in the viscosity. It is also mentioned that during longer storage periods, slight separations might occur which can be eliminated by stirring.

Polyol fatty acid esters are often used as viscosity adjusters in the production of pearlizing concentrates. It was proposed in the U.S. Pat. No. 5,711,899 to reduce the viscosity of pearlescent concentrates by addition of small amount of low molecular weight polyhydric alcohols and thus to make them flowable and pumpable. The preferred polyhydric alcohol mentioned in this patent is glycerol. Table 2 mentioned in the patent shows a distinct reduction in the viscosity from 22,000 mPa-s to14,000 mPa-s on adding glycerol. Further, these pearlescent concentrates are stable for three months only.

German patent application DE 4103551 (Henkel) describes pearlizing concentrates in the form of flowable aqueous dispersions which contain 15 to 40% by weight pearlizing components, 5 to 55% by weight emulsifiers and 0.1 to 5 or 15 to 40% by weight polyols. Polyhydric alcohols are added in large amount to make them flowable, pumpable and obviating the need of preservatives.

Polyols are also used in European patent application EP 0205922 A2 (Henkel). This application relates to flowable pearlizing concentrates containing 5 to 15% by weight acylated polyglycols, 1 to 6% by weight fatty acid monoethanolamides and 1 to 5% by weight nonionic emulsifiers. According to the teaching of European patent EP 0569843 B1 (Hoechst), nonionic flowable pearlizing dispersions may also be obtained by preparing mixtures of 5 to 30% by weight acylated polyglycols and 0.1 to 20% by weight selected from nonionic surfactants. European patent application EP 0684302 A1 (Th. Goldschmidt) proposes the use of polyglycerol esters as crystallization aids for the production of pearlizing concentrates.

U.S. Pat. No. 7,268,107 (Cognis) describes highly concentrated pearlizing concentrates with a high content of pearlizing waxes and a low content of emulsifiers wherein 0.1 to 5% by weight polyol esters are added to control viscosity.

Patent application WO2004/028676 (Huntsman) talks about the problem of high viscosity, thickening on storage under warm conditions and stability in pearlescent concentrates containing aqueous mixture of amphoteric surfactants and acceptable glycol stearates. For optimum viscosity, the patent application describes use of non-ionic or anionic deflocculents. In addition, the pearlizing concentrates may contain non-ionic dispersants.

JP2008013581 discloses preparation of pearlescent concentrates with low viscosity by using non-ionic surfactants with an HLB value of 9~12. Further, it is mentioned that non-ionic surfactant with an HLB of 15 or more cannot lower the viscosity to the desired flowable & pumpable level.

International patent application WO 94/24248 discloses pearlizing agents based on alkyl polyglycoside/betaine surfactants which also contain glycols.

U.S. Pat. No. 6,306,916 mentions that the pearlescent concentrates prepared by the teachings of U.S. Pat. No. 5,711,899 have pronounced non-Newtonian or thixotropic behavior. The viscosity of non-Newtonian fluids is dependent on shear rate and hence non-Newtonian behavior is unacceptable for pearlescent concentrates. To overcome the non-Newtonian behavior, U.S. Pat. No. 6,306,916 teaches addition of Alkyl polyglycosides to pearlescent concentrates.

Accordingly, there is a need for pearlescent concentrates which have low viscosities and do not exhibit an increase in viscosity during storage and which are suitable for sulfate-free formulations.

The present invention addresses the problem of prior art by providing sulfate-free pearlizing concentrates which prevent viscosity-build up, without addition of polymers or inorganic carriers.

OBJECT OF INVENTION i) It is an objective of the present invention to develop a cold-dispersible pearlescent concentrates of low viscosity that are stable at temperature between 5-40° C.
ii) It is also an objective of this invention to develop a cold-dispersible pearlescent concentrate which has stable rheological properties.
iii) It is another objective of the present invention to develop a cold-dispersible pearlescent concentrate which are free of harsh alkyl sulfates/alkyl ether sulfates.
iv) It is yet another object of the present invention to develop a process for manufacturing free flowing, sulfate-free cold-dispersible pearlescent concentrate with low viscosity.

SUMMARY OF INVENTION

In accordance with the above objectives, the present invention provides aqueous, free flowing cold-dispersible sulfate-free pearlescent concentrates, which comprises;
1. N-acyl glycinate surfactants;
2. Esters of ethylene glycol as pearly wax; and
3. Non-ionic surfactant.

The cold-dispersible, aqueous pearlescent concentrates of the present invention comprises
a) 10 to 15% by weight of N-acyl glycinate (Formula I)

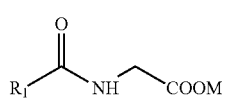

Formula I wherein, $R_1$ is selected from $C_7$ to $C_{17}$ saturated or unsaturated alkyl group and M is a counterion selected from $Na^+$, $K^+$, $NH_4^+$;
b) 15 to 25% by weight of esters of ethylene glycol as pearlizing wax (Formula II)

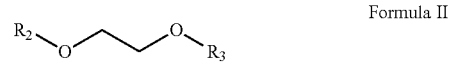

Formula II wherein, $R_2$ is a linear $C_{16}$ to $C_{18}$ fatty acyl group, $R_3$ is H or $R_2$;
c) 2 to 8% by weight of non-ionic surfactant of Formula III

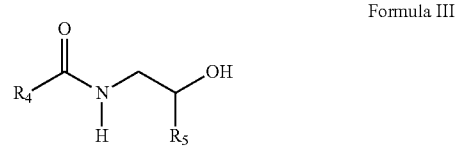

Formula III wherein, $R_4$ is $C_7$ to $C_{17}$ alkyl group, $R_5$ is H or $CH_3$.

All percentages and ratios herein are on weight percent basis unless otherwise stated. The term 'cold' as utilized herein refers to the ability of the concentrate to be added without heating the personal and home care products.

In the second aspect, the present invention is directed to personal care compositions containing the cold-dispersible sulfate-free pearlizer concentrate of the present invention.

DETAILED DESCRIPTION OF INVENTION

The present invention relates to a sulfate-free, cold-dispersible pearlescent concentrate that has low viscosity. The pearlescent compositions of the patent application are stable and there is no viscosity build up during longer storage time.

In the first aspect, the present invention is directed to aqueous, free flowing cold-dispersible sulfate-free pearlescent concentrates, which comprises;
1. N-acyl glycinate surfactants;
2. Esters of ethylene glycol as pearly wax; and
3. Non-ionic surfactant.

The cold-dispersible, aqueous pearlescent concentrates of the present invention comprises;
a) 10 to 15% by weight of N-acyl glycinate (Formula I)

Formula I wherein, $R_1$ is selected from $C_7$ to $C_{17}$ saturated or unsaturated alkyl group and M is a counterion selected from $Na^+$, $K^+$, $NH_4^+$;
b) 15 to 25% by weight of esters of ethylene glycol as pearlizing wax (Formula II)

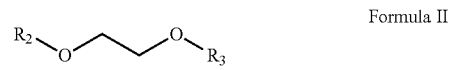

Formula II wherein, $R_2$ is a linear $C_{16}$ to $C_{18}$ fatty acyl group, $R_3$ is H or $R_2$;
c) 2 to 8% by weight of non-ionic surfactant of Formula III

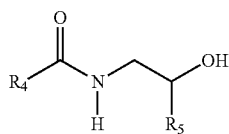

Formula III wherein, $R_4$ is $C_7$ to $C_{17}$ alkyl group, $R_5$ is H or $CH_3$.

In another embodiment, the invention provides a process for manufacture of free flowing cold-dispersible sulfate-free pearlescent concentrates which comprises;
  i) emulsifying pearly wax using N-acyl glycinate surfactant and non-ionic surfactant at 75 to 80° C.;
  ii) cooling the emulsified mass gradually to 45° C. over 2 to 4 hours under gentle agitation;
  iii) adding water at 45° C. followed by cooling to room temperature;
  iv) adjusting the pH to 6 to 7.5 with citric acid; and
  v) adding preservative under stirring.

The viscosity of the pearlescent blends thus obtained is below 4,000 mPas (Table I) and the solids content is kept minimum 35% by weight. The particle size distribution is between 5 to 15 μm ($D_{50}$) when measured using Malvern particle size analyzer (Mastersizer 2000E).

The pearlescent concentrates thus prepared are stable at temperatures as low as 5° C. and can be stored at a temperature of from 5° C. to about 40° C. for long periods, i.e. at least about six months, without any significant increase in viscosity (Table I).

TABLE I

| | Stability data of pearlescent concentrates | | | | | | | | | |
|---|---|---|---|---|---|---|---|---|---|---|
| | Initial | Viscosity (mPas) | | | | | | | | |
| | viscosity | 1 Month | | | 2 Months | | | 6 Months | | |
| Exp. | (mPas) | 5° C. | R.T. | 40° C. | 5° C. | R.T. | 40° C. | 5° C. | R.T. | 40° C. |
| L# 465 | 2000 | 1500 | 2000 | 2500 | 1000 | 2000 | 4000 | 1000 | 2000 | 4000 |
| L# 468 | 1500 | 1500 | 1500 | 2000 | 1000 | 1500 | 3000 | 1000 | 1500 | 4000 |
| P # 01 | 2000 | 1500 | 2000 | 2500 | 1500 | 2000 | 2000 | 1500 | 2000 | 2000 |
| P # 02 | 1500 | 1000 | 1500 | 2500 | 1000 | 1500 | 2000 | 1500 | 1500 | 2000 |

The cocoyl cut alkyl chain distribution for N-cocoyl glycinate is given in TABLE II.

TABLE II

| Carbon chain distribution of Cocoyl group | |
|---|---|
| Carbon chain | Range |
| $C_8$ | 4-12% |
| $C_{10}$ | 4-14% |
| $C_{12}$ | 59-65% |
| $C_{14}$ | 14-24% |
| $C_{16}$ | 1-8% |
| $C_{18}$ | 0.5 to 12% |

The preservative is selected from phenoxy ethanol, undecylenoyl glycine, capryloyl glycine, glyceryl undecylenate, glyceryl caprylate, 2-ethylhexyl glycerol, dehydro acetic acid, benzoic acid or mixtures thereof.

In an embodiment, the non-ionic surfactant is selected from cocomonoethanol amide, cocomonoisopropanol amide or capryloyl-caproyl (C8-10) glycine.

The aqueous, cold-dispersible pearlescent concentrates of the present invention can be formulated into a wide variety of personal care and home care products by merely mixing the personal or home care products together with the concentrate at room temperature. These aqueous, cold processable pearlescent concentrates can be added to personal care and home care compositions in an amount ranging from 2-10% by weight.

These concentrates are used for imparting pearlescence to sulfate-free formulations (Examples 6, 7 & 8). These products can be formulated by one skilled in the art utilizing conventional methods of preparation. The pearlizing concentrate of the instant invention imparts a high luster, nacreous look to body-wash, face-wash and shampoo (Examples 6, 7 & 8).

ADVANTAGES OF THE INVENTION

1. The pearlescent concentrates of the present invention have low viscosity and therefore easy to handle and transport.
2. These concentrates are of stable rheology over a broad range of temperature ranging from 5-40° C. for 6 months.
3. These pearlescent concentrates can be specifically used for sulfate-free formulations.
4. These compositions are free from harsh fatty alcohol sulfates & fatty alcohol ether sulfates (SLES). It should also be noted that all commercially available SLES contain 1,4-dioxane which is reported to be carcinogenic in animal.
5. The cold-dispersible pearlescent concentrates of the present invention avoids usage of controversial, estrogeinic, carcinogenic, incompatible antimicrobials e.g. parabens or formaldehyde releasers, phenolic, halogenated and quaternary ammonium type of molecules for the purpose of preservation.

EXAMPLES

The present invention is now described by way of working non-limiting illustrative examples. The detail of the invention provided in the following examples is given by the way of illustration only and should not be construed to limit the scope of the present invention.

Example 1: Preparation of Cold-Dispersible Sulfate-Free Pearlizing Blend with Ethylene Glycol Distearate (EGDS)

| Ingredients | Qty (g) |
|---|---|
| Sodium cocoyl glycinate (30% aq. solution) | 468 |
| Cocomonoethanol amide (CMEA) | 67 |
| Ethylene glycol distearate | 190 |
| Water | 261 |
| Citric acid | 6 |
| Preservative (2-phenoxy ethanol, capryloyl glycine and undecylenoyl glycine in the ratio of 8:1:1) | 8 |
| Total Solids | 411 |
| Weight of total batch | 1000 |

To a stirred solution of sodium cocoyl glycinate (468 g of 30% aqueous solution, 23.5% active with 5% sodium chloride) was added cocomonoethanol amide (CMEA) (67 g) and the resulting mixture was heated to 80° C. for 15 minutes. To this mixture at 80° C., ethylene glycol distearate (190 g) was added and stirred for additional 30 minutes. The resultant emulsion was then slowly cooled to 45° C. over two hours with gentle stirring. To this dispersion, water (261 mL) was added and mass was cooled to room temperature under gentle stirring over a period of two hours. pH was adjusted to 6 to 7.5 using citric acid. It was preserved with a 0.8% blend comprising 2-phenoxy ethanol, capryloyl glycine and undecylenoyl glycine in the ratio of (8:1:1).
Analysis:
  Solids content: 41.1%
  Viscosity at 25° C. Brookfield LV 4, rpm 12: 2500 cps
  pH (10% dispersion): 6.9
  Sodium chloride content: 2.3%

Example 2: Preparation of Cold-Dispersible Sulfate-Free Pearlizing Blend with Ethylene Glycol Monostearate (EGMS)

| Ingredients | Qty (g) |
|---|---|
| Sodium cocoyl glycinate (30% aq. solution) | 425 |
| Cocomonoetahnol amide | 50 |
| Ethylene glycol monostearate (EGMS) | 190 |
| Water | 321 |
| Citric acid | 6 |
| Preservative (2-phenoxy ethanol, capryloyl glycine and undecylenoyl glycine in the ratio of 8:1:1) | 8 |
| Total solids | 381 |
| Weight of total batch | 1000 |

To a stirred solution of sodium cocoyl glycinate (425 g of 30% aqueous solution, 24% active with 5% sodium chloride), was added cocomonoethanol amide (50 g) and the whole mass was heated to 80° C. for 15 mins. To this dispersion at 80° C., ethylene glycol monostearate (190 g) was added and stirred for additional 30 minutes. The resultant emulsion was the slowly cooled to 45-48° C. over two hours with gentle stirring. To this emulsion, water (321 mL) was added and mass was cooled to room temperature under gentle stirring over a period of two hours. pH was adjusted to 6 to 7.5 using citric acid. It was preserved with a 0.8% blend comprising 2-phenoxy ethanol, capryloyl glycine and undecylenoyl glycine in the ratio of (8:1:1).
Analysis:
  Solids content: 38.1%
  Viscosity at 25° C. Brookfield LV 4, rpm 12: 3000 cps
  pH (10% dispersion): 6.7
  Sodium chloride content: 2.1%

Example 3: Preparation of Cold-Dispersible Sulfate-Free Pearlizing Blend with Sodium Cocoyl Glycinate (SCG), Capryloyl-Caproyl (C8-10) Glycine & Ethylene Glycol Distearate (EGDS)

| Ingredients | Qty (g) |
|---|---|
| Sodium cocoyl glycinate (30% aq. Solution) | 425 |
| Capryloyl-caproyl glycine | 50 |
| Ethylene glycol distearate | 190 |
| Water | 323 |
| Citric acid | 4 |
| Preservative (2-phenoxy ethanol, capryloyl glycine and undecylenoyl glycine in the ratio of 8:1:1) | 8 |
| Total solids | 380 |
| Total Batch | 1000 |

To a stirred solution of sodium cocoyl glycinate (425 g of 30% aqueous solution, 24% active with 5% sodium chloride), was added capryloyl-caproyl glycine (50 g) and the whole mass was heated to 80° C. for 15 mins. To this dispersion at 80° C., ethylene glycol distearate (190 g) was added and stirred for additional 30 minutes. The resultant emulsion was the slowly cooled to 45-48° C. over two hours with gentle stirring. To this emulsion, water (323 mL) was added and mass was cooled to room temperature under gentle stirring over a period of two hours. pH was adjusted to 6 to 7.5 using citric acid. It was preserved with a 0.8% blend comprising 2-phenoxy ethanol, capryloyl glycine and undecylenoyl glycine in the ratio of (8:1:1).
Analysis:
  Solids content: 38%
  Viscosity at 25° C. Brookfield LV 4, rpm 12: 2900 cps
  pH (10% dispersion): 6.1
  Sodium chloride content: 2.1%

Example 4: Preparation of Cold-Dispersible Sulfate-Free Pearlizing Blend with Sodium Lauroyl Glycinate (SLG), Cocomonoethanol Amide (CMEA) & Ethylene Glycol Distearate (EGDS)

| Ingredients | Qty (g) |
|---|---|
| Sodium lauroyl glycinate (30% aq. Solution) | 468 |
| Cocomonoetahnol amide | 50 |
| Ethylene glycol distearate | 190 |
| Water | 278 |
| Citric acid | 6 |
| Preservative (2-phenoxy ethanol, capryloyl glycine and undecylenoyl glycine in the ratio of 8:1:1) | 8 |
| Total solids | 394 |
| Total Batch | 1000 |

To a stirred solution of sodium lauroyl glycinate (468 g of 30% aqueous solution, 24% active with 5% sodium chloride), was added cocomonoethanol amide (50 g) and the whole mass was heated to 80° C. for 15 mins. To this dispersion at 80° C., ethylene glycol distearate (190 g) was added and stirred for additional 30 minutes. The resultant emulsion was the slowly cooled to 45-48° C. over two hours with gentle stirring. To this emulsion, water (278 mL) was added and mass was cooled to room temperature under gentle stirring over a period of two hours. pH was adjusted to 6 to 7.5 using citric acid. It was preserved with a 0.8% blend comprising 2-phenoxy ethanol, capryloyl glycine and undecylenoyl glycine in the ratio of (8:1:1).

Analysis:
 Solids content: 39.4%
 Viscosity at 25° C. Brookfield LV 4, rpm 12: 2500 cps
 pH (10% dispersion): 6.9
 Sodium chloride content: 2.3%

Example 5: Preparation of Cold-Dispersible Sulfate-Free Pearlizing Blend with Sodium Cocoyl Glycinate (SCG), Cocomonoisopropanol Amide (CMIPA) & Ethylene Glycol Distearate (EGDS)

| Ingredients | Qty. (g) |
| --- | --- |
| Sodium cocoyl glycinate (30% aq. Solution) | 468 |
| Cocomonoisopropanol amide | 67 |
| Ethylene glycol distearate | 190 |
| Water | 261 |
| Citric acid | 6 |
| Preservative (2-phenoxy ethanol, capryloyl glycine and undecylenoyl glycine in the ratio of 8:1:1) | 8 |
| Total solids | 411 |
| Total Batch | 1000 |

To a stirred solution of Sodium cocoyl glycinate (468 g of 30% aqueous solution, 24% active with 5% sodium chloride), was added cocomonoisopropanol amide (67 g) and the whole mass was heated to 80° C. for 15 mins. To this dispersion at 80° C., ethylene glycol distearate (190 g) was added and stirred for additional 30 minutes. The resultant emulsion was the slowly cooled to 45-48° C. over two hours with gentle stirring. To this emulsion, water (261 mL) was added and mass was cooled to room temperature under gentle stirring over a period of two hours. pH was adjusted to 6 to 7.5 using citric acid. It was preserved with a 0.8% blend comprising 2-phenoxy ethanol, capryloyl glycine and undecylenoyl glycine in the ratio of (8:1:1).

Analysis:
 Solids content: 41.1%
 Viscosity at 25° C. Brookfield LV 4, rpm 12: 2500 cps
 pH (10% dispersion): 6.9
 Sodium chloride content: 2.3%

Example 6: 'Sulfate-Free' Shampoo

| Ingredients | % (w/w) |
| --- | --- |
| Phase A | |
| Sodium lauroyl sarcosinate (28%) | 20 |
| Sodium cocoyl taurate (40%) | 15 |
| Cocoamidopropyl betaine (29%) | 15 |
| Deionized water | To make 100.0 |
| Phase B | |
| PEG 150 distearate | 1.8 |
| CMEA | 2 |
| Polyquaternium 7 | 2 |
| Pearlescent concentrate of Example 1 | 5 |
| Galguard NK 1 (mixture of 2-phenoxy ethanol & parabens) | 0.5 |

Heated phase A to 70-75° C. and stirred until uniform mass was obtained. Added phase B to phase A and stirred until the mass was homogeneous. The pH of the final formulation was adjusted to 5.8-6.0 with 50% aqueous citric acid solution. The mass was blended with fragrance and color.

Example 7: 'Sulfate-Free' Body Wash

| Ingredients | % (w/w) |
| --- | --- |
| Phase A | |
| Sodium cocoyl sarcosinate (29%) | 10 |
| Alkyl polyglucoside (C8/C10) | 5 |
| Sodium cocoyl taurate (40%) | 20 |
| Cocamidopropyl betaine (29%) | 10 |
| Glycerine | 2 |
| Deionized water | To make 100.0 |
| Phase B | |
| PEG 150 distearate | 1.5 |
| CMEA | 1.2 |
| Pearlescent concentrate of Example 1 | 5 |
| Galguard NK 1(mixture of 2-phenoxy ethanol & parabens) | 0.5 |

Heated phase A to 70-75° C. and stirred until uniform mass was obtained. Added phase B to phase A and stirred until the mass was homogeneous. The pH of the final formulation was adjusted to 5.8-6.0 with 50% aqueous citric acid solution. The mass was blended with fragrance and color.

Example 8: Mild Face Wash

| Ingredients | % (w/w) |
| --- | --- |
| Phase A | |
| Disodium laureth sulfosuccinate | 15.00 |
| Cocamidopropyl betaine | 15.00 |
| Sodium lauroyl sarcosinate | 10.00 |
| PEG-7 glyceryl cocoate | 2 |
| Glycerin | 5.00 |
| Deionized water | To make 100.0 |
| Phase B | |
| PEG-150 distearate | 1.5 |
| Pearlescent concentrate of Example 1 | 5.0 |
| Galguard NK 1(mixture of 2-phenoxy ethanol & parabens) | 0.5 |

Heated phase A to 70-75° C. and stirred until uniform mass was obtained. Added phase B to phase A and stirred until the mass was homogeneous. The pH of the final formulation was adjusted to 5.8-6.0 with 50% aqueous citric acid solution. The mass was blended with fragrance and color.

We claim:

1. A free flowing, cold-dispersible, aqueous pearlescent concentrate having a viscosity of less than 4000 mPas at 25° C., comprising;
   a) 10 to 15% by weight of an N-acyl glycinate of Formula I:

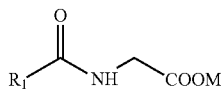
   Formula I

Wherein, $R_1$ is selected from the group consisting of $C_7$ to $C_{17}$ saturated or unsaturated alkyl groups and M is an alkali metal or ammonium counterion;
   b) 15 to 25% by weight of esters of ethylene glycol as a pearlizing wax of Formula II:

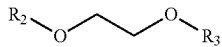
   Formula II wherein $R_2$ is a linear $C_{16}$ to $C_{18}$ fatty acyl group, and $R_3$ is H or $R_2$; and
   c) 2 to 8% by weight of non-ionic surfactant of Formula III:

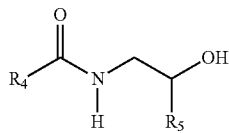
   Formula III wherein $R_4$ is a $C_7$ to $C_{17}$ alkyl group, and $R_5$ is H or $CH_3$; and wherein said concentrate is free of sulfates and quaternary ammonium compounds.

2. The pearlescent concentrate according to claim 1, wherein said concentrate is stable at a temperature between 5° C. and 40° C.

3. The pearlescent concentrate according to claim 1, wherein said concentrate has a solids content of at least 35% by weight.

4. The pearlescent concentrate according to claim 1, wherein said concentrate has a $D_{50}$ particle size of 5-15 μm.

5. A process for preparing the pearlescent concentrate according to claim 1 comprising;
   i) emulsifying said pearlizing wax of Formula II with said N-acyl glycinate and said non-ionic surfactant at a temperature of between about 75° C. and about 80° C. to produce an emulsified mass;
   ii) cooling the emulsified mass to a temperature of about 45° C.;
   iii) adding water to the emulsified mass at a temperature of about 45° C. followed by cooling to room temperature;
   iv) adjusting the pH to between 6 and 7.5; and
   v) adding a preservative under stirring.

* * * * *